United States Patent [19]

Carlock

[11] 4,178,313
[45] Dec. 11, 1979

[54] OLEFIN ISOMERIZATION AND HYDROFORMYLATION PROCESS

[75] Inventor: John T. Carlock, Ponca City, Okla.

[73] Assignee: Conoco, Inc., Ponca City, Okla.

[21] Appl. No.: 924,601

[22] Filed: Jul. 14, 1978

[51] Int. Cl.² .............................................. C07C 45/08
[52] U.S. Cl. .............................................. 260/604 HF
[58] Field of Search .................. 260/604 HF; 568/909

[56] References Cited

U.S. PATENT DOCUMENTS

| | | | |
|---|---|---|---|
| 3,847,997 | 11/1974 | Allen | 260/604 HF |
| 4,052,461 | 10/1977 | Tinker et al. | 260/604 HF |

*Primary Examiner*—Werren B. Lone

*Attorney, Agent, or Firm*—Cortlan R. Schupbach, Jr.

[57] ABSTRACT

Olefins are converted to aldehydes in the presence of a catalyst having the general formula

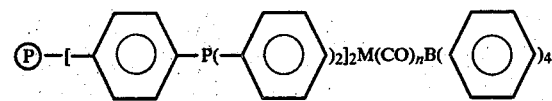

wherein M is rhodium or iridium, ⓟ is a polyvinyl-pyridine/dimethylbenzene copolymer, and n is 1 to 3. Internal olefins are isomerized in appreciable extent to primary olefins, then hydroformylated to primary aldehydes.

5 Claims, No Drawings

OLEFIN ISOMERIZATION AND HYDROFORMYLATION PROCESS

This invention relates to the isomerzation of olefins and hydroformylation of said olefins to aldehydes. More particularly, this invention relates to the use of a bis(triphenylphosphine) metal tris(carbonyl) tetraphenylborate complexed with diphenylphosphinated crosslinked polystyrene to yield a catalyst capable of isomerizing internal olefins and hydroformylating all classes of olefins to aldehydes.

The hydroformylation of terminal (or alpha) olefins by certain homogeneous rhodium catalysts is known in the art. Representative examples of references describing homogeneous rhodium catalysts used in hydroformylation reactions and reaction conditions necessary are found in U.S. Pat. Nos. 3,917,661; 3,907,847; 3,821,311; 3,499,932; 2,527,809; 3,825,601; 3,948,999; and 3,984,478. Polymerbound rhodium literature references include Tetrahedron Letters, 1971 (50) 4787-90, Grubbs et al; Journal of Macroml. Sci. Chem., 1972, 13 (12) 828-32. While these references are not exhaustive of the art, they appear to be representative of hyroformylation in the current state of the art. However, these catalysts and reactions are generally very poor when dealing with internal olefins. When these catalysts are dissolved in the reaction mixture the catalysts are difficult to recover. Recovery of the catalyst are important since rhodium is an extremely expensive metal and the product cost rises sharply with each percentage drop in rhodium recovery from a previous reaction.

Hydroformylation is a reaction which converts olefins equivalent to alkenes for the purposes of this specification and claims to aldehydes. Usually the hydroformylation procedure is followed by the hydrogenation of aldehydes to produce alcohol. However, the hydrogenation procedure is relatively simple and can be carried out by any one of several well known means. In this procedure of converting olefins to alcohols, the most difficult and least efficient step is the initial hydroformylation conversion of olefins to aldehydes.

U.S. Pat. Nos. 3,636,159 and 3,652,676 also describe polymer-bound hydroformylation catalysts. However, these references deal with catalysts in reactions which are carried out under severe conditions for lengthy reaction times. In addition, these catalysts deal with primary olefins only.

U.S. Pat. No. 4,052,461, hereby incorporated by reference, deals with the preparation of aldehydes by hydroformylation of olefins using a rhodium catalyst complexed with ligands other than halides and non-coordinating anions, and at least 2 moles of a modifying ligand per mole of ionic rhodium compound, said modifying ligand being a tertiary organophosphorus compound. This reference provides a method of preparation for the active component of the catalyst of the instant invention. The patent distinctly states that the catalysts described are non-isomerizing with regard to the olefins. In addition, it has been found that bis(triphenylphosphine) rhodium tris (carbonyl) tetraphenylborate [abbreviated (BRCB) for the purposes of this invention] is inactive or fails to promote hydroformylation catalysis with internal olefins. Further, this material is difficult to recover from reaction mixtures, this recovery being important since rhodium is an extremely expensive metal.

Since internal olefins are available from many sources and since these materials are generally much less expensive and reactive than primary olefins, it would be greatly desirable to provide a catalyst which isomerizes internal olefins to alpha olefins and then hydroformylates the alpha olefins thus obtained in such a way as to yield linear aldehydes. In addition, it would be desirable to provide a catalyst which does not require a solvent for reaction procedures, and which is easily recoverable.

It is therefore an object of the instant invention to provide a catalyst which will isomerize internal olefins to alpha olefins and hydroformylate the olefins obtained to linear aldehydes in the absence of a solvent. Other objects will become apparent to those skilled in this art as the description proceeds.

It has now been discovered according to the instant invention that when a catalyst having the general structure

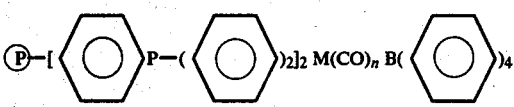

is formed by reacting bis(triphenylphosphine) rhodium tris(carbonyl) tetraphenylborate (BRCB) or bis(triphenylphosphine) iridium tris(carbonyl) tetraphenyl borate (BICB) in a complex with a diphenyl phosphenated cross-linked polystyrene that all classes of olefins are converted to aldehydes at temperatures of from about 60° to about 150° C. and hydrogen/carbon monoxide pressures of from about 50 to about 3500 psig, wherein Ⓟ is a diphenylphosphinated cross-linked polystyrene, M is rhodium or iridium, and n is 1 to 3. In addition, this material is substantially active in the isomerization of internal olefins to primary olefins prior to their subsequent hydroformylation to aldehydes. The catalysts are easily recoverable and are stable under any inert gas.

The present catalysts are a distinct advantage over those described in the prior art. It is surprising that the complexing of prior art catalysts to the diphenyl phosphinated cross-linked polystyrene would provide the changes in catalyst activity discovered. For example, BRCB as described in U.S. Pat. No. 4,052,461 must be stored under an atmosphere of carbon monoxide to prevent decomposition. Such storage requirements are not only inconvenient but represent a potential personnel health hazard due to the toxicity of carbon monoxide. In contrast, the catalysts of the instant invention can be stored under any inert gas without decomposing. Secondly, BRCB is inactive or fails to promote hydroformylation catalysis with internal olefins. In distinct contrast, the catalysts of the instant invention substantially isomerize internal olefins to primary olefins before hydroformylating such olefins to linear primary aldehydes. In addition, BRCB is difficult to recover from reaction mixtures. Such recovery is greatly simplified by complexing to the polymer since the catalyst system become heterogeneous and recovery can be made by simple filtration under an inert atmosphere. Finally, BRCB must be used with a solvent which necessitates extra processing steps to purify the product from said solvent. No solvent is necessary with the catalysts of the instant invention, although if circumstances dictate, solvent can be used.

It is distinctly surprising that all these advantages can be gained by complexing BRCB to a highly cross-linked diphenylphosphinated polystyrene. In addition, it has been discovered that when iridium is used in place of rhodium, (BICB) that similar results will occur. These catalysts can be used in a neat or non-solvent state in olefins under carbon monoxide/hydrogen atmospheres, producing pure aldehyde products and presenting no solvent removal problem.

Normally the hydroformylation will be carried out at temperatures of from about 60° to about 150° C. although preferred temperatures are from about 80° to about 130° C. and most preferred temperatures are about 100° C.

The reaction is carried out under an atmosphere of carbon monoxide and hydrogen at pressures of from about 50 to about 3500 psig. However, normal pressures will range from about 300 to about 1,000 psig and most preferred pressures are from about 300 to about 400 psig. In carrying out the typical hydroformylation reaction to produce aldehydes, it is necessary to supply 1 mole of carbon monoxide and 1 mole of hydrogen for each mole of olefin reaction. Excess carbon monoxide or hydrogen over these amounts can be present. Normally, the ratio of hydrogen to carbon monoxide will range from 1:100 to 100:1 respectively, although from about 80:20 to about 20:80 respectively is preferred, and from about 60:40 to about 50:50 respectively is more preferred and 50:50 respectively is most preferred.

The catalysts of the instant invention are recoverable and reuseable by simple means such as filtration. Filtration is carried out under an inert atmosphere. The catalysts in addition to acting as oxo (or hydroformylation) catalyst can be used to hydrogenate aldehydes and other types of unsaturated organic compounds such as alkene, alkynes, and aromatic rings to their saturated analogues.

The instant invention is more concretely described with reference to the examples below wherein all parts and percentages are by weight unless otherwise specified. The examples are provided to exemplify the instant invention and not to limit it.

In all examples which follow, as well as catalyst transfers, a humidity controled argon atmosphere dry box was used, employing flame dried glassware. All solvents were of an anhydrous grade. BRCB was synthesized according to the process described in U.S. Pat. No. 4,052,461.

EXAMPLE 1

Polystyrene cross-linked polymer (XAD-4, trademark of and sold by Rhom and Haas Corp.) was diphenylphosphinated according to the method described in *Journal of Organic Chemistry*, 41, 3877 (1976), Farrall et al; and *Journal of the American Chemical Society*, 94, 1789 (1972); Collman et al. Phosphorus analysis of the diphenylphosphinated polystyrene by x-ray fluorescence showed phosphorus be present in 2.4% level by weight. The reaction vessel of a Parr shaker apparatus was charged with 36 grams of the diphenylphosphinated polymer, 5 grams of bis(triphenylphosphine) rhodium tris(carbonyl) tetraphenylborate and 50 (ml) of tetrahydrofuran (THF). The Parr shaker apparatus was connected to a source of carbon monoxide. The reaction vessel was pressured to 28 pounds per square inch gauge (psig) carbon monoxide, and the mixture agitated by the shaking apparatus for 24 hours. The contents of the reaction vessel were filtered, then continuously extracted with benzene for 24 hours while being maintained under a flow pressure of 24 psig at 300 ml per minute of carbon monoxide. The polymeric catalyst so obtained was then dried at 25° C. in vacuum for 18 hours. A salmon-colored product (31 grams) was isolated which gave the following analysis: rhodium 0.93%, boron 0.5%; phosphorus 2.1%; and oxygen 1.3%.

EXAMPLE 2

A general method for the use of the catalyst in autoclave reactions is illustrated. Two grams (g) of the polymeric catalyst were charged into a magnetically stirred autoclave with 30 g of 1-tetradecene and 5.0 grams of n-dodecene (used as a vapor phase chromatographic internal standard). The reactor was purged three times to 400 psig with a 1:1 hydrogen carbon monoxide gas mixture, vented completely so that all gauges indicated no internal pressure and heated to 100° C. At 100° C. an internal reactor pressure of 25 psig was indicated. A 1:1 hydrogen/carbon monoxide mixture of 300 psig was added, giving a total pressure of 325 psig. After 4.45 hours of reaction time, chemical analysis of the reaction mixture by GLC indicated an 80% conversion of 1-tetradecene to $C_{15}$ aldehydes having a normal to branched ratio of 2.20. The catalyst was separated from the reaction mixture by filtration under argon.

EXAMPLE 3

The catalyst recovered from Example 2 was recharged into the autoclave and an identical reaction as that described in Example 2 was carried out except that the reaction temperature was lowered to 95° C. and the 1:1 hydrogen carbon monoxide gas pressure employed was reduced to 200 psig. After 6 hours of reaction time, chemical analysis of the reaction mixture indicated a 75% conversion of 1-tetradecene to $C_{15}$ aldehydes having a normal to branched product ratio of 2.60. Thus it is apparent that milder reaction conditions give higher normal to branched ratios but result in lower conversion.

EXAMPLE 4

The catalyst was recovered from Example 3 by filtration under an inert atmosphere and a reaction identical to Example 3 was carried out except that the reaction temperature was reduced to 90° C. and the hydrogen carbon monoxide pressure maintained at 150 psig. After 7.72 hours of reaction time, chemical analysis of the reaction product indicated a 63% conversion of 1-tetradecane to $C_{15}$ aldehydes having a normal to branched product ratio of 3.15. Thus the reaction results confirm those of Example 3.

EXAMPLE 5

The catalyst was recovered from Example 4 by filtration under an inert atmosphere and a reaction identical to Example 3 was carried out except that the olefin feedstock consisted of 30 grams of 7-tetradecene. The reaction temperature was maintained at 115° C. and the 1:1 hydrogen carbon monoxide gas pressure was increased to 900 psig. After 12.25 hours of reaction time, chemical analysis of the reaction mixture indicated an 80% conversion of 7-tetradecene to $C_{15}$ aldehydes. Further analysis of the aldehyde product by gas liquid chromatography (GLC) and $C_{13}$ nuclear magnetic resonance (NMR) indicated that a 35% olefin isomerization had taken place resulting in a 2% formation of n-pentadecanal. Thus the isomerization potential of the polymerbound catalyst is illustrated.

EXAMPLE 6

The catalyst was recovered from Example 5 by filtration under an inert atmosphere and recharged into an autoclave. A reaction identical with Example 5 was carried out except that the olefin feedstock consisted of a thermal distribution mixture of 30 grams of $C_{11}$ and $C_{12}$ olefins, the reaction temperature was maintained at 120° C. and the 1:1 hydrogen carbon monoxide pressure was 925 psig. After 19/½ hours of reaction time, chemical analysis of the reaction mixture indicated that a 74% conversion of $C_{11}$ and $C_{12}$ olefins to $C_{12}$ and $C_{13}$ aldehydes had occurred. Further analysis by gas liquid chromatography and $C_{13}$ NMR of the aldehyde product indicated that 7.6% of the aldehydes were either n-dodecanal or n-tridecanal, again illustrating that isomerization potential of the catalyst.

EXAMPLE 7

Metal elution from the polymer was quantified by x-ray fluorescence technique. The aldehyde products from each reaction being sampled and tested for rhodium. A summary of each reaction together with the elution results are shown in Table 1.

mixture and vented to 0 psig. The autoclave is then heated to 120° C. and at this temperature the reactor is pressurized with 950 psig of 1:1 $H_2$/CO. After an appropriate period of reaction time the autoclave contents will show a substantial conversion of 7-tetradecene to $C_{15}$ aldehydes.

Any polystyrene can be used in the instant invention. However, if the polystyrene used is not sufficiently crosslinked, a swelling solvent is necessary during the reaction to provide acceptable reation rates. Examples of suitable solvents are benzene, dimethylsulfoxide, tetrahydrofuran, toluene, xylene and acetophenone. "Highly-crosslinked" designates a crosslinking above about 20%. These catalysts are suitable for use in fixed-bed continuous reactors.

A surprising method has been discovered for the isomerization of internal olefins to primary aldehydes. The reaction is carried out in the absence of solvents and the catalyst is recoverable for use in subsequent reactions. The catalysts are recovered largely in tact except for a normal handling losses due to filtration techniques. Rhodium elution appears to have little effect upon catalyst activity, reaction conditions being more significant.

While certain embodiments and details have been shown for the purpose of illustrating this invention, it

Table 1

| Example No. | Sequence No. | Substrate | Product | % Conv./ Time Hr. | n/i | Psig/° C. | Rh Elution (PPM) |
|---|---|---|---|---|---|---|---|
| 2 | 1 | 1-tetradecene | $C_{15}$ aldehydes | 80/4.45 | 2.20 | 300/100 | 14 |
| 3 | 2 | 1-tetradecene | $C_{15}$ aldehydes | 75/6.00 | 2.60 | 200/95 | 4.2 |
| 4 | 3 | 1-tetradecene | $C_{15}$ aldehydes | 63/7.71 | 3.15 | 150/90 | 4.5 |
| 5 | 4 | 7-tetradecene | $C_{15}$ aldehydes | 80/12.25 | — | 900/115 | 2.4 |
| 6 | 5 | $C_{11}$–$C_{12}$ internal olefin mixture | $C_{12}+C_{13}$ aldehydes | 74/19.5 | — | 920/120 | 3.1 |

EXAMPLE 8

Two grams of catalyst is charged into an autoclave with 35 grams of 7-tetradecene. The reactor is purged 5 times to 300 psig with pure hydrogen and vented back to 0 psig. The autoclave is then heated to 110° C. and pressured to 950 psig $H_2$ at the temperature. After an appropriate period of reaction time analysis of the autoclave contents reveal significant conversion of 7-tetradecene to n-tetradecane.

EXAMPLE 9

To a methanol solution (100 ml) in an argon or other inert atmosphere containing 16 g of $Ph_3P$ (61 mmoles) is added 2.0 g of $(Ir(COD)CL)_2$ where COD is an abbreviation of 1,5-cyclooctadiene and the mixture is stirred. After 30 minutes of 316 g of $NaBPh_4$ (10.5 mmoles) is added and the suspension again stirred for 30 minutes. The fine yellow precipitate is washed with ether and dried. A solution of 100 ml of acetone containing 10 g of this fine yellow precipitate is treated with CO and concentrated to a volume of 10 ml. Crystallization from the acetone is accomplished by the addition of ethanol. The product is filtered and washed with ether in a CO atmosphere. This isolated compound is then equilibrated with diphenylphosphinated polystyrene and processed identically as in Example 1 to heterogenize the iridium catalyst.

Two grams of this catalyst are charged into an autoclave along with 35.0 grams of 7-dodecene. The reaction is purged three times to 900 psig with a 1:1 $H_2$/CO mixture and vented to 0 psig. The autoclave is then heated to 120° C. and at this temperature the reactor is pressurized with 950 psig of 1:1 $H_2$/CO. After an appropriate period of reaction time the autoclave contents will show a substantial conversion of 7-tetradecene to $C_{15}$ aldehydes.

will be apparent to those skilled in this art that various changes and modifications may be made herein without departing from the spirit or scope of the invention.

I claim:

1. A method for converting olefins to aldehydes wherein said olefins are converted to aldehydes in the presence of a catalyst having the general structure

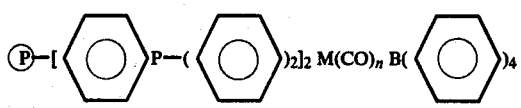

said conversions carried out at temperatures of from about 60° to about 150° C. and hydrogen/carbon monoxide pressures of from about 50 to about 300 psig wherein Ⓟ is a diphenylphosphinated cross-linked polystyrene, M is rhodium or iridium, and n is 1 to 3.

2. A method as described in claim 1 wherein M is rhodium.

3. A method as described in claim 2 wherein n is 3.

4. A method as described in claim 2, wherein internal olefins are isomerized to primary olefins, then hydroformylated to aldehydes in the presence of a catalyst having the general structure

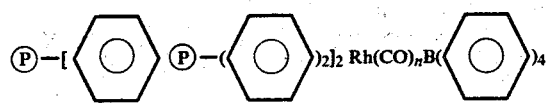
said isomerization and hydroformylation being carried out at temperatures of from about 60° to about 150° C. and pressure of from about 50 to about 3500 psig wherein Ⓟ is the same and n is from 1 to 3.
5. A method as described in claim 4 when carried out continuously in a fixed-bed reactor.
* * * * *